United States Patent [19]

Herrling

[11] 4,305,887

[45] Dec. 15, 1981

[54] PROCESS FOR OBTAINING THE ENANTIOMERIC FORMS OF 4-CYANO-1-[N-METHYL-N-(2'-{3'',4''-DIMETHOXYPHENYL}-ETHYL)-AMINO]-5-METHYL-4-(3',4',5'-TRIMETHOXYPHENYL)-HEXANE AND OF SALTS THEREOF

[75] Inventor: Siegfried Herrling, Stolberg, Fed. Rep. of Germany

[73] Assignee: BASF Aktiengesellschaft, Fed. Rep. of Germany

[21] Appl. No.: 204,954

[22] Filed: Nov. 7, 1980

[30] Foreign Application Priority Data

Nov. 11, 1979 [DE] Fed. Rep. of Germany ....... 2946545

[51] Int. Cl.$^3$ ............................................. C07C 121/78
[52] U.S. Cl. ............................ 260/465 E; 260/465 D
[58] Field of Search ..................................... 260/465 E

[56] References Cited

U.S. PATENT DOCUMENTS 3,261,859  7/1966  Dengel ............................ 260/465 E

FOREIGN PATENT DOCUMENTS 1154810   9/1963  Fed. Rep. of Germany .
1158083  11/1963  Fed. Rep. of Germany .
2059923   6/1972  Fed. Rep. of Germany .
2059985   6/1972  Fed. Rep. of Germany .
1069921   5/1967  United Kingdom .
1367677   9/1974  United Kingdom .
1377209  12/1974  United Kingdom .

OTHER PUBLICATIONS

Helv. Chim. Acta, 58 (1975), pp. 2050–2060.

*Primary Examiner*—Dolph H. Torrence
*Attorney, Agent, or Firm*—Keil & Witherspoon

[57] ABSTRACT

A process for obtaining the enantiomeric forms of 4-cyano-1-[N-methyl-N-(2'-{3'',4''-dimethoxyphenyl}-ethyl)-amino]-5-methyl-4-(3',4',5'-trimethoxyphenyl)-hexane and of its salts, in which the acid salt of the compound with an optically active form of O,O'-dibenzoyltartaric acid is first prepared, as a diastereomer mixture, by neutralizing the free base or by double decomposition of another salt of the compound, and the mixture is then separated by crystallization. Thereafter, the pure diastereomers thus obtained are converted to the free bases of the enantiomeric forms, or to salts thereof, in a conventional manner.

3 Claims, No Drawings

PROCESS FOR OBTAINING THE ENANTIOMERIC FORMS OF 4-CYANO-1-[N-METHYL-N-(2'-{3'',4''-DIMETHOXYPHENYL}-ETHYL)-AMINO]-5-METHYL-4-(3',4',5'-TRIMETHOXYPHENYL)-HEXANE AND OF SALTS THEREOF

German Pat. Nos. 1,154,810 and 1,158,083 describe the preparation of certain phenylacetonitriles which possess a basic substituent and which have, for example, the following formula

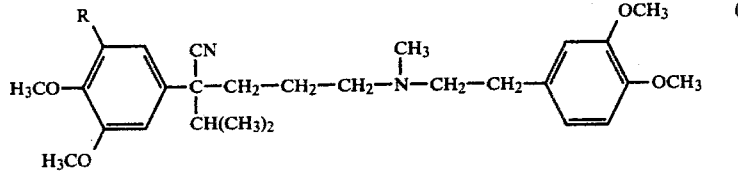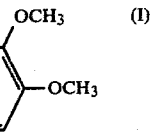

where R is hydrogen or methoxy, in their racemic form. It has not proved possible to obtain the optically active forms of the compound where R is hydrogen by resolution of the racemate (Helv. chim. Acta, 58 (1975) 2050 et seq.), so that a multi-stage synthesis, from optically active starting materials, has been developed for obtaining the enantiomers of this compound.

German Pat. No. 2,059,923 describes, inter alia, the preparation of the l-form of the compound of the formula I, where R is hydrogen, by multi-stage processes, which in every case use optically active starting materials.

German Pat. No. 2,059,985 relates, inter alia, to certain dextro-rotary phenylacetonitriles which have a basic substituent, and to processes for their preparation; some of the products conform to the above formula I. This publication, like those quoted earlier, again involves, in every case, preparation of the optically active compounds by multi-stage syntheses using optically active starting materials.

Accordingly, this prior art necessarily led to the supposition that separation of the racemate is impossible in the case of phenylacetonitriles carrying certain substituents, in particular in the case of compounds of the formula I.

I have found, surprisingly, that the enantiomers of 4-cyano-1-[N-methyl-N-(2'-{3'',4''-dimethoxyphenyl}-ethyl)-amino]-5-methyl-4-(3',4',5'-trimethoxyphenyl)-hexane (I, R=CH₃O, hereafter referred to as Compound Ia) and their salts can be obtained, in good yield, from the racemate of Compound Ia by first preparing the acid salt from this compound and one mole of an optically active form, preferably the D-form, of 0,0'-dibenzoyltartaric acid, separating the diastereomeric forms of this salt by crystallization and then obtaining therefrom, in a conventional manner, the free base of the Compound Ia in the enantiomeric form, or a different salt thereof, for example the hydrochloride.

The acid salt of the optically active form of 0,0'-dibenzoyltartaric acid with Compound Ia is prepared by double decomposition (for example reaction of the monosodium salt of (+)-0,0'-dibenzoyl-(D)-tartaric acid with the hydrochloride of Compound Ia) or by neutralizing the free base with free (+)-0,0'-dibenzoyl-(D)-tartaric acid in the presence of a suitable solvent, for example a lower alcohol, especially isopropanol.

The d-form of Compound Ia possesses powerful anti-arrhythmic properties without causing inotropic side effects, whilst the l-form possesses a pronounced coronary action at doses at which it produces at most very slight, if any, anti-arrhythmic effects.

The Examples which follow illustrate the invention. All temperature data are uncorrected. In carrying out these Examples, no attention was given to optimizing the yields.

EXAMPLE 1

(a) 26 g of d,l-4-cyano-1-[N-methyl-N-(2'-{3'',4''-dimethoxyphenyl}-ethyl)-amino]-5-methyl-4-(3',4',5'-trimethoxyphenyl)-hexane hydrochloride (Ia) are dissolved in 500 ml of 50% strength ethanol (ie. a mixture of equal parts by volume of ethanol and water) and a solution of 18.8 g of (+)-0,0'-dibenzoyl-D-tartaric acid hydrate and 2 g of sodium hydroxide in 50 ml of 50% strength ethanol is added, whilst stirring. The mixture is stirred for 1½ hours at room temperature and is then kept in a refrigerator for 15 hours. The crystals which have precipitated are filtered off, dried and then recrystallized twice from isopropanol or from 60% strength ethanol. This gives the acid (+)-0,0'-dibenzoyl-D-tartrate of the d-form of Compound Ia in a yield of 17.4 g=83% of theory; $[\alpha]_D^{22} = +69.2°$ (10.6 mg/ml of ethanol); melting point: 123° C. These values do not change on further recrystallization.

(b) 17 g of the salt obtained in Example 1a are vigorously stirred or shaken with 100 ml of toluene and 80 ml of 1 N sodium hydroxide solution until the salt has been decomposed and the mixture forms two clear layers on being left to stand. These layers are separated and the toluene layer is washed with water and then treated with a mixture of 50 ml of 1 N hydrochloric acid and 25 ml of water. The precipitate is filtered off and dissolved, with gentle warming, in the hydrochloric acid layer which has been separated from the toluene layer. The solution is filtered and then kept refrigerated for a few hours. The precipitate is filtered off, washed with a small amount of ice water and then dried azeotropically with toluene. Repeated recrystallization from isopropanol gives d-4-cyano-1-[N-methyl-N-(2'-{3'',4''-dimethoxyphenyl}-ethyl)-amino]-5-methyl-4-(3',4',5'-trimethoxyphenyl)-hexane hydrochloride as a white crystalline powder, in a yield of 41.6% of theory (based on the initial amount of the product from Example 1a); $[\alpha]_D^{22} = +13.3°$ (12 mg/ml of ethanol); melting point: 159°–161° C.

EXAMPLE 2

(a) The ethanol-containing mother liquor obtained in Example 1a is concentrated to a small volume under reduced pressure and is then cooled. The crystals which have precipitated are filtered off, washed with water and then recrystallized from ethyl acetate, giving the acid (+)-0,0'-dibenzoyl-D-tartrate of the l-form of Compound Ia. Yield: 10.2 g=48.5% of theory; $[\alpha]_D^{22} = +47.9°$ (9.82 mg/ml of ethanol); melting point: 87°–90° C.

(b) 10 g of the salt obtained in Example 2a are treated in accordance with the procedure described in Example 1b, giving 1-4-cyano-1[N-methyl-N-(2'-{3'',4''-dimethoxyphenyl}-ethyl)-amino]-5-methyl-4-(3',4',5'-trimethoxyphenyl)-hexane hydrochloride as a white crystalline powder, in a yield of 2.8 g (=45.3% of theory); $[\alpha]_D^{20} = -13.4°$ (10.6 mg/ml of ethanol); melting point: 158°–161° C.

EXAMPLE 3

(a) 24.23 g of d,l-4-cyano-1-[N-methyl-N-(2'-{3'',4''-dimethoxyphenyl}-ethyl)-amino]-5-methyl-4-(3',4',5'-trimethoxyphenyl)-hexane (Ia) are dissolved in 75 ml of isopropanol and a solution of 18.82 g of (+)-0,0'-dibenzoyl-D-tartaric acid hydrate in 50 ml of isopropanol is then added, whilst stirring. The mixture is kept in a refrigerator overnight. The crystals are filtered off and then recrystallized twice from isopropanol. The same product as in Example 1a is obtained, in a yield of 18.1 g = 86% of theory. It can be reacted further as described in Example 1b.

(b) The first mother liquor obtained in Example 3a is concentrated under reduced pressure. The residue is recrystallized from ethyl acetate, giving the same product as described in Example 2a. Yield: 13.7 g = 65% of theory.

EXAMPLE 4

The procedure described in the preceding Examples is followed, but instead of (+)-0,0'-dibenzoyl-D-tartaric acid hydrate, 18.82 g of (−)-0,0'-dibenzoyl-L-tartaric acid hydrate are used; once again, the d- and l-forms of the hydrochloride of 4-cyano-1-[N-methyl-N-(2'-{3'',4''-dimethoxyphenyl}-ethyl)-amino]-5-methyl-4-(3',4',5'-trimethoxyphenyl)-hexane are obtained.

EXAMPLE 5

The procedure described in Example 1b is followed, but instead of aqueous hydrochloric acid, a solution of about 0.9 g of hydrogen chloride in moist ether is added to the water-washed toluene layer containing the product. The precipitate is filtered off and dissolved in 0.5 N hydrochloric acid at about 40°–50° C. This hydrochloric acid solution is kept in a refrigerator for several hours. The precipitate is isolated, and treated further, as described in Example 1b, giving the desired product in a yield of 48.5% of theory (based on the initial amount of the product from Example 1a).

I claim:

1. A process for obtaining the enantiomeric forms of 4-cyano-1-[N-methyl-N-(2'-{3'',4''-dimethoxyphenyl}-ethyl)-amino]-5-methyl-4-(3',4',5'-trimethoxyphenyl)-hexane and of its salts, wherein the acid salt of the compound with an optically active form of 0,0'-dibenzoyltartaric acid is prepared, as a diastereomer mixture, by neutralizing the free base or by double decomposition of another salt of the compound, and the mixture is separated by crystallization, and the pure diastereomers thus obtained are converted in a conventional manner to the free enantiomeric forms of 4-cyano-1-[N-methyl-N-(2'-{3'',4''-dimethoxyphenyl}-ethyl)-amino]-5-methyl-4-(3',4',5'-trimethoxyphenyl)-hexane or to salts thereof.

2. A process as claimed in claim 1, wherein the diastereomer mixture of the acid 0,0'-dibenzoyltartrate is prepared using isopropanol as the solvent.

3. A process as claimed in claim 1 or 2, wherein (+)-0,0'-dibenzoyl-D-tartaric acid, its hydrate or one of its mono-alkali metal salts is used.

* * * * *